United States Patent
Ross et al.

(10) Patent No.: US 9,987,034 B2
(45) Date of Patent: Jun. 5, 2018

(54) ULTRASONIC SURGICAL SYSTEM HAVING A FLUID COOLED BLADE AND RELATED COOLING METHODS THEREFOR

(71) Applicant: COVIDIEN LP, Mansfield, MA (US)

(72) Inventors: Anthony B. Ross, Boulder, CO (US); Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Arlen K. Ward, Thornton, CO (US)

(73) Assignee: COVIDIEN LP, Mansfield, MA (US)

( * ) Notice: Subject to any disclaimer, the term of this patent is extended or adjusted under 35 U.S.C. 154(b) by 334 days.

(21) Appl. No.: 14/642,958

(22) Filed: Mar. 10, 2015

(65) Prior Publication Data

US 2015/0173791 A1 Jun. 25, 2015

Related U.S. Application Data

(62) Division of application No. 13/236,768, filed on Sep. 20, 2011, now Pat. No. 8,974,478.

(51) Int. Cl.
*A61B 17/32* (2006.01)
*A61B 17/34* (2006.01)
(Continued)

(52) U.S. Cl.
CPC .. *A61B 17/320068* (2013.01); *A61B 17/3211* (2013.01); *A61B 17/3474* (2013.01);
(Continued)

(58) Field of Classification Search
CPC .......... A61B 2017/22027; A61B 2017/22024; A61B 2017/22021; A61B 17/2202;
(Continued)

(56) References Cited

U.S. PATENT DOCUMENTS

| 2,990,616 A | 7/1961 | Balamuth |
| 3,053,124 A | 9/1962 | Balamuth |

(Continued)

FOREIGN PATENT DOCUMENTS

JP    2000237204 A    9/2000

OTHER PUBLICATIONS

European Search Report dated Mar. 26, 2015, issued in European Application No. 12184991.

*Primary Examiner* — Thomas McEvoy

(57) ABSTRACT

The present disclosure is directed to a fluid cooled ultrasonic surgical instrument and related systems and methods of use therefor. In some embodiments, the disclosed ultrasonic surgical instrument is adapted for used within an insufflated cavity or pneumoperitoneum of a patient. The instrument includes a housing having an elongate shaft, a waveguide disposed at a distal end of the shaft, a coolant inlet port defined in an outer surface of the housing, and a coolant pump disposed within the housing and configured to move coolant from the coolant inlet port to the waveguide. During use, insufflation gas from within the pneumoperitoneum is drawn into the instrument shaft by the coolant pump, and blown over the waveguide to provide cooling. The delivery of ultrasonic energy and activation of the pump may be controlled by a processor in response to user input and waveguide temperature.

19 Claims, 7 Drawing Sheets

(51) Int. Cl.
*A61B 17/3211* (2006.01)
*A61B 17/22* (2006.01)
*A61B 17/00* (2006.01)

(52) U.S. Cl.
CPC ............ *A61B 2017/00106* (2013.01); *A61B 2017/22021* (2013.01); *A61B 2017/320084* (2013.01)

(58) Field of Classification Search
CPC ........... A61B 2017/22018; A61B 2017/22015; A61B 2017/22014; A61B 17/22012; A61B 2017/22011; A61B 17/22004; A61B 17/320068; A61B 2017/320096; A61B 17/320092; A61B 2017/320088; A61B 2017/320084; A61B 2017/32008; A61B 2017/320076; A61B 2017/320072
See application file for complete search history.

(56) References Cited

U.S. PATENT DOCUMENTS

| | | | |
|---|---|---|---|
| 3,086,288 A | 4/1963 | Balamuth | |
| 3,805,787 A | 4/1974 | Banko | |
| 4,063,557 A | 12/1977 | Wuchinich et al. | |
| 4,223,676 A | 9/1980 | Wuchinich et al. | |
| 4,425,115 A | 1/1984 | Wuchinich | |
| 4,526,571 A | 7/1985 | Wuchinich | |
| 5,163,421 A | 11/1992 | Bernstein et al. | |
| 5,190,517 A | 3/1993 | Zieve et al. | |
| 5,306,999 A | 4/1994 | Hoffman | |
| 5,344,435 A | 9/1994 | Turner et al. | |
| 5,412,304 A | 5/1995 | Abbott | |
| 5,484,398 A | 1/1996 | Stoddard | |
| 5,498,236 A | 3/1996 | Dubrul et al. | |
| 5,499,185 A | 3/1996 | Tanzer et al. | |
| 5,919,219 A | 7/1999 | Knowlton | |
| 6,214,017 B1* | 4/2001 | Stoddard ........ A61B 17/320068 606/128 |
| 6,215,281 B1 | 4/2001 | Koch | |
| 6,241,700 B1 | 6/2001 | Leukanech | |
| 6,241,753 B1 | 6/2001 | Knowlton | |
| 6,518,727 B2 | 2/2003 | Oomura et al. | |
| 6,547,904 B1 | 4/2003 | Young | |
| 6,575,969 B1 | 6/2003 | Rittman, III et al. | |
| 6,579,811 B2 | 6/2003 | Narwankar et al. | |
| 6,689,087 B2 | 2/2004 | Pal et al. | |
| 6,719,755 B2 | 4/2004 | Sliwa, Jr. et al. | |
| 6,832,998 B2 | 12/2004 | Goble | |
| 7,137,963 B2 | 11/2006 | Nita et al. | |
| 7,160,259 B2 | 1/2007 | Tardy et al. | |
| 7,167,741 B2 | 1/2007 | Torchia et al. | |
| 7,186,246 B2 | 3/2007 | Bennett et al. | |
| 7,211,084 B2 | 5/2007 | Goble et al. | |
| 7,238,166 B2 | 7/2007 | Callister | |
| 7,270,656 B2 | 9/2007 | Gowda et al. | |
| 7,294,127 B2 | 11/2007 | Leung et al. | |
| 7,540,852 B2 | 6/2009 | Nita et al. | |
| 7,572,257 B2 | 8/2009 | Whayne et al. | |
| 7,776,032 B2 | 8/2010 | Stoller et al. | |
| 8,444,664 B2 | 5/2013 | Balanev et al. | |
| 8,662,745 B2 | 3/2014 | Misuchenko et al. | |
| 8,974,478 B2 | 3/2015 | Ross et al. | |
| 2003/0201053 A1 | 10/2003 | Young | |
| 2005/0209578 A1 | 9/2005 | Evans et al. | |
| 2005/0273127 A1 | 12/2005 | Novak et al. | |
| 2007/0161945 A1 | 7/2007 | Nita et al. | |
| 2007/0232913 A1 | 10/2007 | Lau et al. | |
| 2007/0239027 A1 | 10/2007 | Nita | |
| 2007/0239062 A1 | 10/2007 | Chopra et al. | |
| 2007/0239075 A1 | 10/2007 | Rosenberg et al. | |
| 2007/0260172 A1 | 11/2007 | Nita | |
| 2007/0265560 A1 | 11/2007 | Soltani et al. | |
| 2007/0265609 A1 | 11/2007 | Thapliyal et al. | |
| 2007/0265610 A1 | 11/2007 | Thapliyal et al. | |
| 2008/0221562 A1 | 9/2008 | Garabedian et al. | |
| 2008/0319376 A1 | 12/2008 | Wilcox et al. | |
| 2009/0036914 A1 | 2/2009 | Houser | |
| 2009/0082794 A1 | 3/2009 | Finlay et al. | |
| 2009/0187137 A1 | 7/2009 | Volz et al. | |
| 2009/0312692 A1* | 12/2009 | Cotter ............ A61B 17/320068 604/22 |
| 2010/0137751 A1* | 6/2010 | Tadami ............ A61B 18/1402 601/2 |
| 2012/0249060 A1 | 10/2012 | Stoddard et al. | |
| 2012/0253328 A1 | 10/2012 | Cunningham et al. | |
| 2012/0253370 A1 | 10/2012 | Ross et al. | |
| 2012/0253371 A1 | 10/2012 | Ross et al. | |
| 2012/0253372 A1 | 10/2012 | Ross et al. | |
| 2012/0310229 A1 | 12/2012 | Gregg | |
| 2013/0030328 A1 | 1/2013 | Dycus et al. | |
| 2013/0085419 A1 | 4/2013 | Stoddard et al. | |
| 2013/0197511 A1 | 8/2013 | Balanev et al. | |
| 2013/0325047 A1 | 12/2013 | Craig | |

\* cited by examiner

ULTRASONIC SURGICAL SYSTEM HAVING A FLUID COOLED BLADE AND RELATED COOLING METHODS THEREFOR

CROSS-REFERENCE TO RELATED APPLICATION

This application is a divisional of and claims the benefit of, and priority to, U.S. patent application Ser. No. 13/236,768, which was filed on Sep. 20, 2011, the entire contents of which is hereby incorporated by reference.

BACKGROUND

Technical Field

The present disclosure relates generally to surgical instruments, and in particular, to an ultrasonic dissector having fluid-cooled components and related methods of cooling components of an ultrasonic surgical instrument.

Background of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy may be delivered to tissue using a surgical probe that includes a transducer coupled with an end effector, and configured to deliver ultrasonic energy to tissue.

The use of ultrasonic energy in surgical procedures is known to those skilled in the art to be a valuable resource for cutting and fragmenting tissue of a patient. Most of these apparatus incorporate a sinusoidal driving signal which causes the mechanical tip of a waveguide to vibrate at a selected frequency, usually in the range of 20 KHz to 60 KHz.

The benefits associated with the use of ultrasonic energy powered devices, and in particular, ultrasonic instruments for surgical use, are known. For example, the use of an ultrasonic generator in conjunction with a surgical scalpel facilitates faster and easier cutting of organic tissue while accelerating coagulation. Improved cutting may result from increased body tissue-to-scalpel contact caused by the high frequency of vibration of the scalpel blade in relation to body tissue. Improved coagulation may result from heat generated by contact between the high frequency vibrations of a scalpel blade and body tissue.

Ultrasonic instruments may include any of a variety of waveguides configured to achieve a surgical result. An ultrasonic waveguide is disposed at a distal end of the ultrasonic instrument. A waveguide may include an end effector that includes a cutting blade, shears, a hook, and/or a ball, each adapted for specific medical procedures, and may be combined with other features such as jaws for grasping or manipulating tissue. Such ultrasonic instruments are primarily used in a variety of medical procedures including open surgical procedures, luminal procedures and endoscopic procedures. During use, waveguides on ultrasonic dissection devices can reach temperatures greater than 200° C. If an overheated waveguide is touched to tissue, the tissue can be damaged.

SUMMARY

The present disclosure is directed to an ultrasonic instrument having a shaft, a waveguide blade at a distal end of the shaft, and one or more cooling ducts disposed at a distal end of the shaft and configured to direct a cooling fluid to the waveguide. The cooling fluid may include air, $CO_2$, and/or saline, which are commonly available in a surgical environment and possess the thermal mass necessary to effectively cool a waveguide, blade, or other component of an ultrasonic instrument. Also disclosed is a coolant delivery unit adapted to deliver fluid to the instrument that may include, without limitation, a fan, an impeller, a pump, a syringe, or a bellows. The coolant delivery unit may be internal or external to the ultrasonic instrument. The coolant delivery unit may be activated automatically, or under control of a surgeon. The coolant delivery unit may also be operatively associated with a temperature sensor and/or activated at one or more predefined temperatures. The cooling fluid may also aid in cleaning the tip of the device and/or the surgical field. In some embodiments, the cooling fluid may be stored for use within a reservoir that is external to the instrument. In some embodiments, the instrument is configured to utilize fluid contained an insufflated cavity within a patient, such as, without limitation, a pneumoperitoneum.

The disclosed device and related methods may have advantages, including without limitation, by enabling the ultrasonic blade(s) to cool more quickly, by preventing collateral damage to surrounding tissue, by allowing surgeons to work more quickly without waiting for the blade to cool, and by allowing the device to be used as a grasper or for other tissue manipulations due to the decreased temperature of the blade and/or other tissue-contacting components.

In accordance with an embodiment of the present disclosure, an ultrasonic surgical instrument is presented that includes a housing having an elongated shaft, a waveguide disposed at a distal end of the shaft, a coolant inlet port defined in an outer surface of the housing, and a coolant pump disposed within the housing and configured to move coolant from the coolant inlet port to the waveguide. The disclosed ultrasonic instrument may include a coolant outlet conduit in fluid communication at a proximal end thereof with a coolant pump outlet. A distal end of the coolant outlet conduit may be configured to direct coolant towards at least a portion of the waveguide. One or more sensors may optionally be operably coupled to the waveguide to sense a property, including without limitation, a temperature, a frequency, an impedance, a phase, an amplitude, a rate of fluid flow, and a quantity of fluid. In some embodiments, the coolant inlet port may be radially aligned with a coolant pump inlet. The coolant pump may include an electric motor.

In accordance with another embodiment of the present disclosure, an ultrasonic surgical system is presented. The disclosed ultrasonic surgical system includes an ultrasonic surgical instrument adapted to operably couple to an ultrasonic generator. The instrument includes a housing having an elongated shaft, a waveguide disposed at a distal end of the shaft, a coolant inlet port defined in an outer surface of the housing, and a coolant pump disposed within the housing and configured to move coolant from the coolant inlet port to the waveguide. The system further includes an ultrasonic generator adapted to operably couple to the ultrasonic instrument. The ultrasonic generator includes an ultrasonic driver unit configured to provide ultrasonic energy to the waveguide, and a coolant activation unit configured to provide a coolant activation signal to the coolant pump.

The ultrasonic surgical instrument may include a sensor operably coupled to the waveguide, and the ultrasonic generator may include a sensor interface unit configured to receive a sensor signal from the sensor. The sensor may be adapted to sense a property selected from the group consisting of a temperature, a frequency, an impedance, a phase, an amplitude, a rate of fluid flow, and a quantity of fluid.

The ultrasonic generator may include a processor in operable communication with at least one of the ultrasonic driver unit, the coolant activation unit, or the sensor interface unit, and may additionally or alternatively include a memory unit in operable communication with the processor. The memory may include any suitable form of data storage device, including without limitation, read-only memory, flash memory, semiconductor memory, optical memory, and/or magnetic memory. The memory unit may include a set of programmed instructions executable on the processor to perform a method of receiving an activation signal, activating the ultrasonic driver unit, and activating the coolant activation unit. The memory may additionally include programmed instructions executable on the processor to perform the steps of receiving a sensor signal corresponding to a temperature of the ultrasonic surgical instrument, and deactivating the ultrasonic driver unit in response to a determination that the temperature of the ultrasonic surgical instrument has exceeded a temperature threshold for a predetermined duration of time.

Also disclosed is a method of cooling an ultrasonic surgical instrument. The disclosed method includes the steps of insufflating a body cavity of a patient with insufflation media, introducing an ultrasonic surgical instrument into the insufflated body cavity, activating delivery of ultrasonic energy to the ultrasonic surgical instrument, and moving the insufflation media through the ultrasonic surgical instrument to cool the ultrasonic surgical instrument. The insufflation media may be selected from the group consisting of carbon dioxide, oxygen, air, and saline. The insufflation media may be moved through the ultrasonic surgical instrument at a rate in accordance with a temperature of the ultrasonic surgical instrument.

The disclosed method may include the steps of sensing a temperature of the ultrasonic surgical instrument, determining whether the sensed temperature exceeds a predetermined temperature threshold, and moving the insufflation media through the ultrasonic surgical instrument at a rate in accordance with the predetermined temperature threshold. The disclosed method may additionally or alternative include the steps of sensing a temperature of the ultrasonic surgical instrument, determining whether the sensed temperature has exceeded a temperature threshold for a predetermined period of time, and moving the insufflation media through the ultrasonic surgical instrument at a rate in accordance with the predetermined temperature threshold in response to a determination that the sensed temperature has exceeded a temperature threshold for a predetermined duration of time. In another aspect the disclosed method includes the steps of sensing a temperature of the ultrasonic surgical instrument, determining whether the sensed temperature has exceeded a temperature threshold for a predetermined period of time, and deactivating delivery of ultrasonic energy to the ultrasonic surgical instrument in response to a determination that the sensed temperature has exceeded a temperature threshold for a predetermined duration of time.

BRIEF DESCRIPTION OF THE DRAWINGS

Various embodiments of the subject instrument are described herein with reference to the drawings wherein.

DETAILED DESCRIPTION

Figure 1:
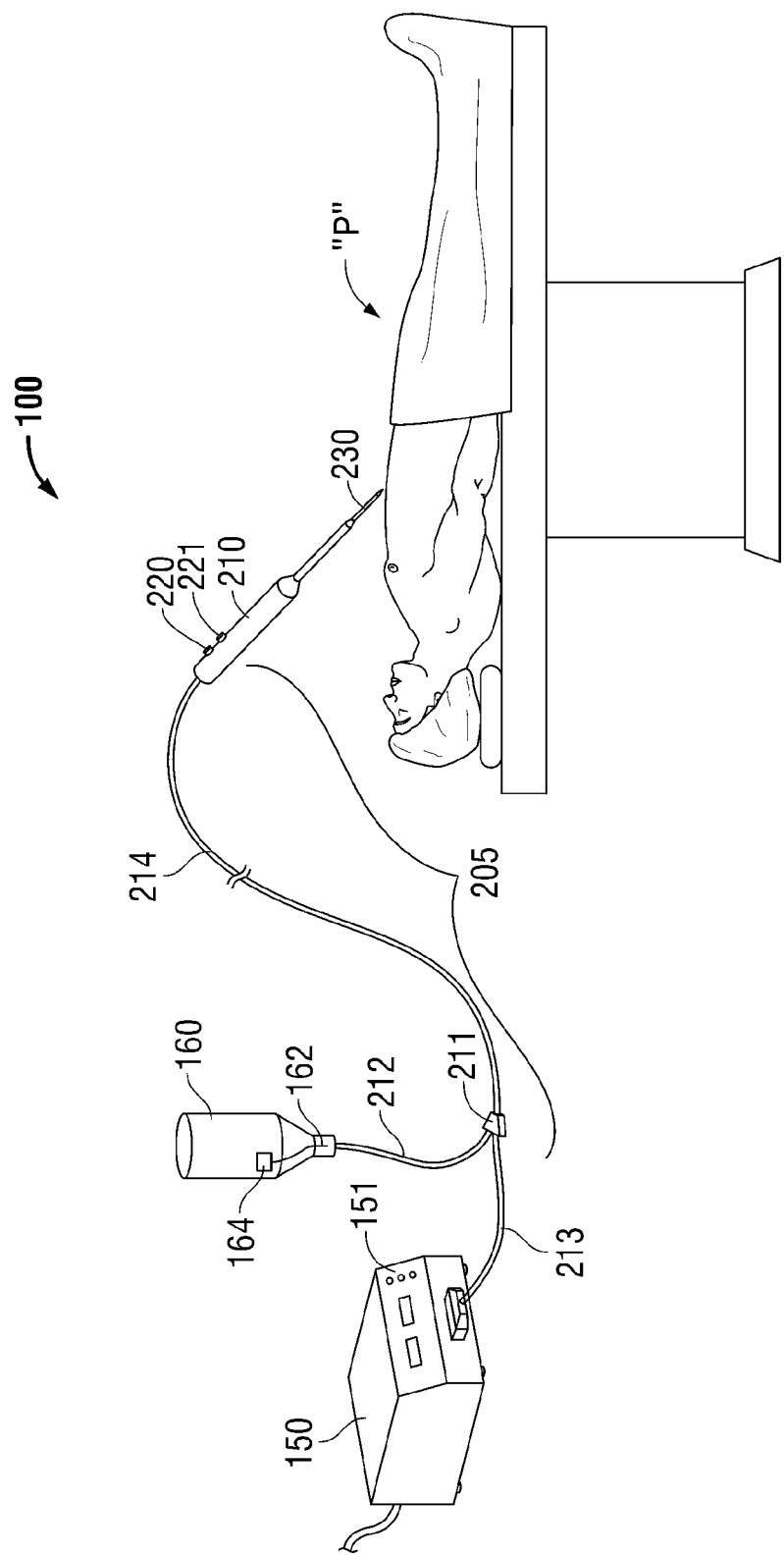
FIG. 1 is a schematic view of an embodiment of a fluid cooled ultrasonic surgical system in accordance with the present disclosure.

Particular embodiments of the present disclosure are described hereinbelow with reference to the accompanying drawings; however, it is to be understood that the disclosed embodiments are merely examples of the disclosure, which may be embodied in various forms. The terminology used herein is for the purpose of describing particular embodiments only, and is not intended to be limiting. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In the drawings and in the descriptions that follow, In the drawings and in the descriptions that follow, the term "proximal," as is traditional, shall refer to the end of the instrument that is closer to the user, while the term "distal" shall refer to the end that is farther from the user. Terms referencing orientation, e.g., "top", "bottom", "up", "down", "left", "right", and the like, are used for illustrative purposes with reference to the figures and features shown therein. It is to be understood that embodiments in accordance with the present disclosure may be practiced in any orientation without limitation. In this description, as well as in the drawings, like-referenced numbers represent elements which may perform the same, similar, or equivalent functions.

Referring to FIG. 1, there is shown an embodiment of an ultrasonic surgical system in accordance with the present disclosure. The disclosed system includes a fluid-cooled ultrasonic instrument 210 that is operatively coupled to an ultrasonic generator 150 and a coolant source 160. As shown, ultrasonic instrument 210 is coupled to generator 150 and a coolant source 160 by a cable assembly 205. Instrument 210 may include one or more controls 220 configured to activate the delivery of ultrasonic energy, activate the delivery of coolant, and/or adjust an operational parameter of the system 100. Instrument 210 includes a waveguide 230, e.g., an end effector, a blade, and the like, for performing an ultrasonic surgical procedure, e.g., dissection, debriding, tissue removal, coagulation, and so forth. Instrument 210 may include one or more indicators 221 configured to provide visual or tactile indications to a user, and may include, without limitation, a light-emitting diode (LED), liquid crystal display (LCD), and/or a shutter indicator. Cable assembly 205 may include a junction 211 that operatively joins a fluid conduit 212 and an electrical cable 213 to cable 214. Electrical cable 213 includes one or more conductors, e.g., electrical conductors, fiber optic conductors, and the like, that are configured to convey ultrasonic energy, control signals, and sensor signals between generator 150 and instrument 210 as described herein. Fluid conduit 212 includes one or more lumens configured to distribute coolant between coolant source 160 and instrument 210, and may optionally include one or more electrical conductors configured to convey electrical signals between coolant source 160, generator 150, and/or instrument 210. Cable 214 may include electrical conductors, fiber optic conductors, and/or coolant lumens in any combination.

Generator 150 includes a user interface 151 having one or more indicators and/or controls in any suitable combination. Coolant source 160 may include a coolant pump 162 to facilitate the flow of coolant between coolant source 160 and instrument 210. Additionally or alternatively, coolant source 160 may include one or more sensors 164 that are adapted to sense a property of coolant and/or of coolant source 160, for example without limitation, coolant level, coolant pressure, coolant temperature, coolant type, and the like.

During use, waveguide 230 of instrument 210 may be brought into contact with a patient P. Generator 150 may be activated to cause ultrasonic excitation of wave guide 230, which, in turn, delivers energy to patient tissue to achieve a surgical objective, e.g., dissection, coagulation, vessel sealing, and the like.

Figure 2:
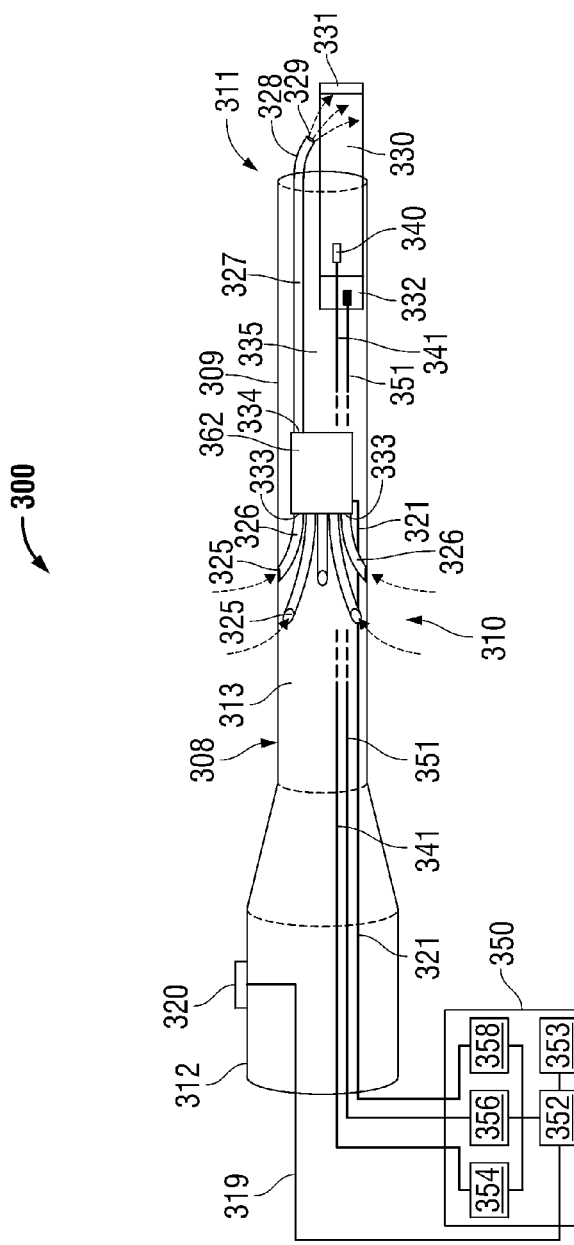
FIG. 2 is an internal view of an embodiment of a fluid cooled ultrasonic surgical instrument in accordance with the present disclosure.
Figure 3:
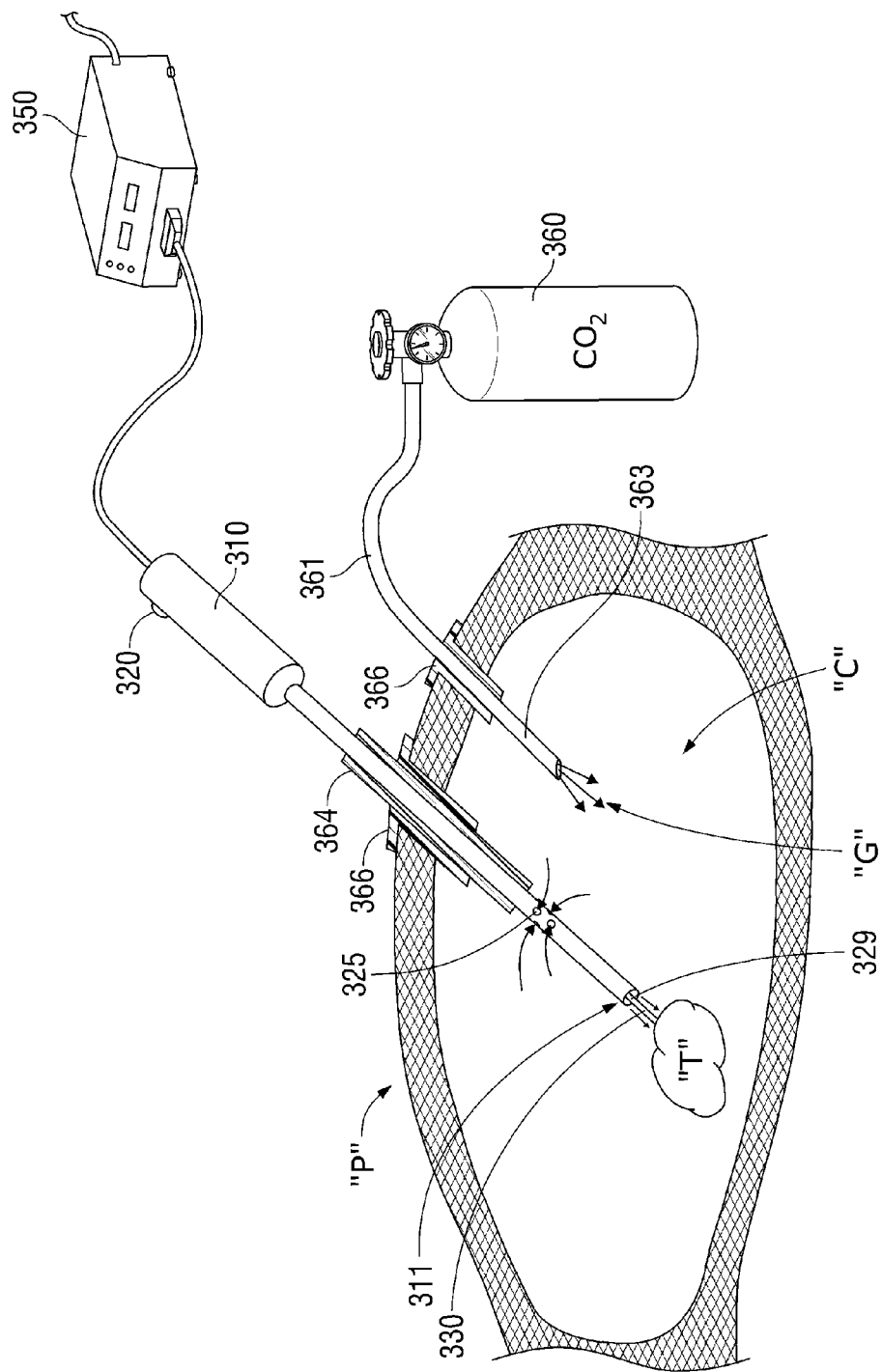
FIG. 3 is a schematic view of an embodiment of a fluid cooled ultrasonic surgical instrument in use in an insufflated surgical field in accordance with the present disclosure.

Turning to FIGS. 2 and 3, an embodiment of an ultrasonic surgical system 300 in accordance with the present disclosure includes an ultrasonic instrument 310 configured to operatively couple with an ultrasonic generator 350. Instrument 310 includes a housing 308 having an elongated shaft 309 and a handle 312 disposed at a proximal end of the shaft. Handle 312 is configured to facilitate handling and manipulation by a user, e.g., a surgeon. A control 320 is disposed on an outer surface 313 of instrument 310, e.g., ergonomically disposed on handle 312. Control 320 is configured to operatively couple to a generator 350 by a conductor 319. As described in detail below, control 320 may be assigned to a dedicated purpose function, e.g., to activate ultrasonic energy. In some embodiments, control 320 may be programmable in accordance with a user's preference, e.g., to activate coolant delivery, to adjust energy intensity, to adjust a duty cycle, and so forth. Control 320 may include one or more independent control elements (e.g., one or more pushbuttons, one or more switches, one or more continuous rotary controls, one or more continuous linear controls, and the like).

Instrument 310 includes a waveguide 330 extending from a distal end 311 of shaft 309 that is configured to contact targeted tissue T. Waveguide 300 may be formed from any suitable material, including without limitation, ceramic, aluminum, titanium, silica, and/or combinations thereof. Waveguide 330 may include one or more blade edges 331 that are adapted to facilitate dissection of tissue. A transducer 332 is operably coupled to waveguide 300 and is adapted to receive an ultrasonic signal, e.g., an alternating current electrical signal in the 20 kHz-60 kHz range, from generator 350 and to translate the ultrasonic signal into mechanical (acoustic) vibrations, which, in turn, excite waveguide 300. Transducer 332 may include piezoelectric, voice coil, electrostatic, or any other transduction components suitable for converting the ultrasonic signal into mechanical oscillations required to excite waveguide 300.

Waveguide 330 includes one or more sensors 340 that are configured to sense one or more operational parameters relating to waveguide 330 and/or tissue T. For example, and without limitation, sensor 340 may be configured to sense at least one of a temperature, a frequency, an impedance, a phase, an amplitude, a rate of fluid flow, or a quantity of fluid. One or more sensors 340 are operably coupled to a sensor interface unit 354 that is included in ultrasonic generator 350, as described in detail below.

Figure 2A:
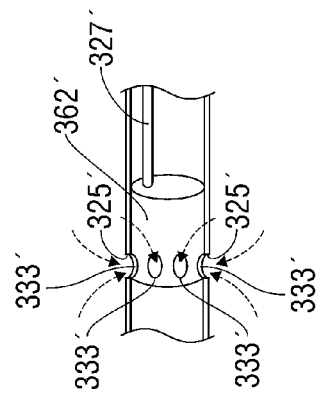
FIG. 2A is a detail internal view of another embodiment of a fluid cooled ultrasonic surgical instrument in accordance with the present disclosure.

Instrument 310 includes a coolant pump 362 that is configured to draw coolant from one or more coolant inlet ports 325 that are disposed on an outer surface of instrument 310. In the FIG. 2 embodiment, coolant pump 362 includes one or more coolant pump inlets 333 disposed on a generally proximal-facing portion of coolant pump 362. Coolant inlet ports 325 are in fluid communication with one or more coolant pump inlets 333 by one or more coolant inlet conduits 326. Additionally or alternatively, as shown in FIG. 2A, coolant pump 362' includes one or more coolant pump inlets 333' arranged radially on a generally outer surface thereof. In the FIG. 2A embodiment, coolant inlet ports 325' defined in an outer surface 313 of instrument 310 are substantially coincident with one or more radial coolant pump inlets 333'.

Coolant pump 362 may employ any suitable pumping technique, including without limitation, at least one of a fan, an axial or radial centrifugal blower, a reciprocating or rotating positive displacement arrangement, or a peristaltic arrangement. Coolant pump 362 may include a motor (not explicitly shown) to provide motive force required to drive the pump. In embodiments, coolant pump 362 may include an electric motor.

Coolant pump 362 includes one or more coolant pump outlets 334 arranged on a generally distal-facing surface of coolant pump 362 that are configured to deliver coolant to a distal end 311 of instrument 310, and, in particular, to deliver coolant to waveguide 330 and/or generally to targeted tissue and an operative field. Instrument 310 may include one or more coolant outlet conduits 327, wherein the one or more coolant pump outlets 334 are in fluid communication with one or more coolant outlet conduits 327 that extend distally from coolant pump 362 to a distal end 311 of instrument 310. In the FIG. 2 embodiment, a distal end 328 of coolant outlet conduit 327 extends beyond a distal end 311 of instrument 310 and is contoured to direct coolant from coolant outlet port 329 toward waveguide 330.

It is to be understood that the present disclosure is not limited to the described arrangement of coolant inlet ports, coolant inlet conduits, coolant pump inlets, coolant pump outlets, coolant outlet conduits, and coolant outlet ports, and that various alternative arrangements of these elements are contemplated within the scope of the present disclosure. For example, and without limitation, in an envisioned embodiment the one or more coolant pump outlets 334 are in fluid communication with an interior region 335 of instrument 310. In this embodiment, interior region 335 is open at a distal end thereof to allow coolant to flow around, e.g., transducer 332, waveguide 330, and to expel coolant from a distal end 311 of instrument 310.

System 300 includes an ultrasonic generator 350 that includes, in operable communication, a processor 352, a memory 353, an ultrasonic driver unit 356, a sensor interface unit 354, and a coolant activation unit 358. Ultrasonic driver unit 356 is operably coupled to transducer 332 by conductor 351. Coolant activation unit 358 is operably coupled to coolant pump 362 by conductor 321. Sensor interface unit 354 is operably coupled to one or more sensors 340 by conductor 341. Memory 353 includes a set of programmed instructions executable on processor 352 to process control data received from control 320, to process a sensor signal received from one or more sensors 340, and/or to control the delivery of ultrasonic energy to transducer 332 and/or waveguide 330, and to control the operation of coolant pump 362. The programmed instructions may include one or more operation profiles, or "modes", that define the relationship between inputs received from control 320 and one or more sensors 340, and outputs transmitted to transducer 332 and/or waveguide 330, and to coolant pump 362.

For example, and without limitation, an operation profile may specify that an actuation of control 320 results in activation of ultrasonic driver unit 356, which, in turn, causes an ultrasonic driver signal to be output therefrom to ultrasonically excite waveguide 330. The operation profile may additionally specify that coolant activation unit 358 be activated concurrently, which, in turn, causes coolant pump 362 to be activated to deliver coolant as described herein.

In some embodiments, coolant activation unit 358 includes the capability to vary the rate at which coolant pump 362 pumps coolant. Additionally or optionally, the rate at which coolant pump 362 operates may vary in accordance with a predetermined coolant delivery profile, and may include a rising portion (e.g., coolant delivery rate increasing over time), a falling portion (e.g., coolant delivery decreasing over time), a steady-state portion, and a deactivated portion.

In other embodiments, ultrasonic driver unit 356 and/or coolant activation unit 358 may be activated in response to an actuation state of control 320 in combination with one or more sensor signals received by sensor interface unit 354 from one or more sensors 340. In this manner, coolant pump 362 speed may be increased in accordance with a change (e.g., increase) in a temperature sensed by one or more sensors 340. Advantageously, an output of ultrasonic driver unit 356 may be modulated in accordance with a sensed temperature. In another non-limiting example, activation of ultrasonic driver unit 356 may be terminated when a sensed temperature exceeds a predetermined threshold. Additionally or alternatively, modulation and/or termination of an ultrasonic driver unit 356 activation may be performed when a sensed temperature exceeds a predetermined threshold for a predetermined length of time.

In another aspect, the disclosed system 300 is adapted for use during minimally-invasive (e.g., laparoscopic) procedures performed within an insufflated surgical field or pneumoperitoneum. As depicted in FIG. 3, instrument 310 is introduced into the body of a patient P using standard interventional techniques. For example, and without limitation, one or more ports 366, which may be a cannula or single-incision laparoscopic surgery (SILS) port, may be inserted into the body of a patient to facilitate access to a body cavity C. A trocar 364 may additionally or alternatively be employed in accordance with surgical objectives. The instrument 310 is introduced into body cavity C. Insufflation gas G is introduced into body cavity C from an insufflation gas source 360 via a conduit 361. Typically, insufflation gas G includes an inert or non-toxic gas, such as, without limitation, carbon dioxide. As depicted in FIG. 3, insufflation gas may be introduced into body cavity C utilizing a port 366 separate from that utilized in connection with instrument 310. In an alternative embodiment, insufflation gas may be introduced utilizing the same port 366 as instrument 310, such as when a SILS port is utilized that enables multiple instruments, conduits, and/or other devices to be inserted into body cavity C through a single, common port 366. In some embodiments, described below, insufflation gas G may be introduced into body cavity C via instrument 310.

Insufflation of body cavity C is typically performed to expand the operative field and/or to mitigate obstructions. After body cavity C is sufficiently insufflated, a distal end 311 of instrument 310 is positioned at the operative site to bring waveguide 330 into surgical engagement with targeted tissue T. A surgeon may then activate generator 350 utilizing, e.g., control 320 of instrument 310, to treat tissue T. Coolant pump 362 may be activated, causing insufflation gas to be drawn in at coolant inlet port(s) 325 and expelled at a distal end 311 of instrument 310 (e.g., via coolant outlet port 329), thereby cooling waveguide 330 and/or tissue at the surgical site. In this manner, an instrument 310 in accordance with the present disclosure advantageously utilizes insufflation gas G available within a body cavity C to achieve improved temperature control (cooling) of the ultrasonic surgical apparatus, which, in turn, may lead to improved operative outcomes, reduced procedure times, and reduced recovery times.

Figure 4:
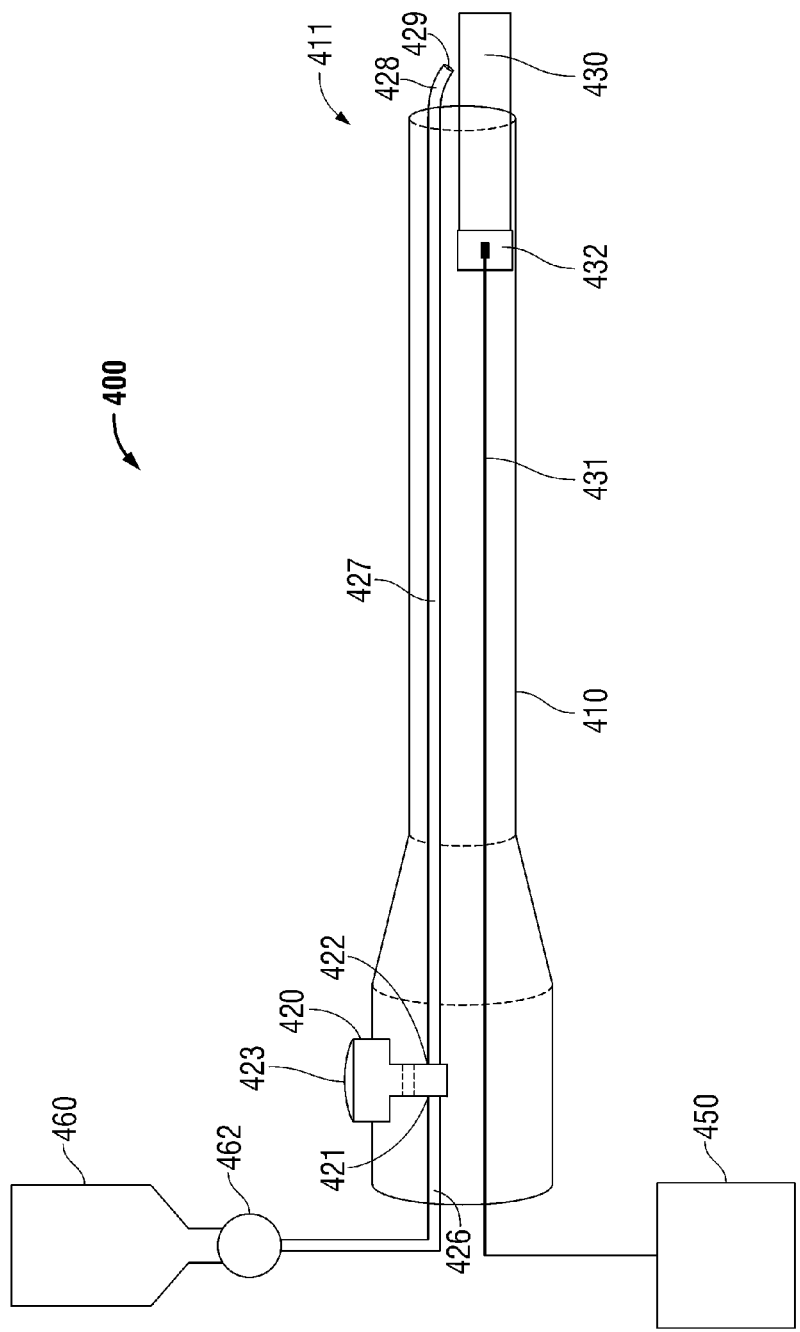
FIG. 4 is an internal view of another embodiment of a fluid cooled ultrasonic surgical instrument in accordance with the present disclosure.

According to another embodiment shown in FIG. 4, an ultrasonic surgical system 400 in accordance with the present disclosure includes an ultrasonic surgical instrument 410 operatively associated with a generator 450 and a coolant source 460. Instrument 410 includes a transducer 432 operatively associated with a waveguide 430, and operatively coupled to generator 450 by conductor 431. A coolant pump 462 is in fluid communication with coolant source 460 and instrument 410 and is configured to pump coolant from coolant supply 460 to instrument 410. Instrument 410 includes a coolant valve 420 that is configured to enable a user to selectively enable the delivery of coolant to waveguide 430 and/or a distal end 411 of instrument 410. As shown, valve 420 includes an inlet 421 in fluid communication with fluid source 460 and/or pump 462 via a coolant supply conduit 426, and an outlet 422 in fluid communication with a distal end 411 of instrument 410 via a fluid outlet conduit 427. A distal end 428 of fluid outlet conduit 428 includes a coolant outlet port 429 that is configured to direct coolant towards waveguide 430. While in the present embodiment valve 420 is illustrated as a gate valve, any suitable valve construction may be incorporated. During use, a user (e.g., surgeon) may enable the flow of coolant by depressing an actuator 423 operatively associated with valve 420. Actuator 423 may be a pushbutton, lever, knob, or any other suitable control for enabling and disabling coolant flow.

Figure 5:
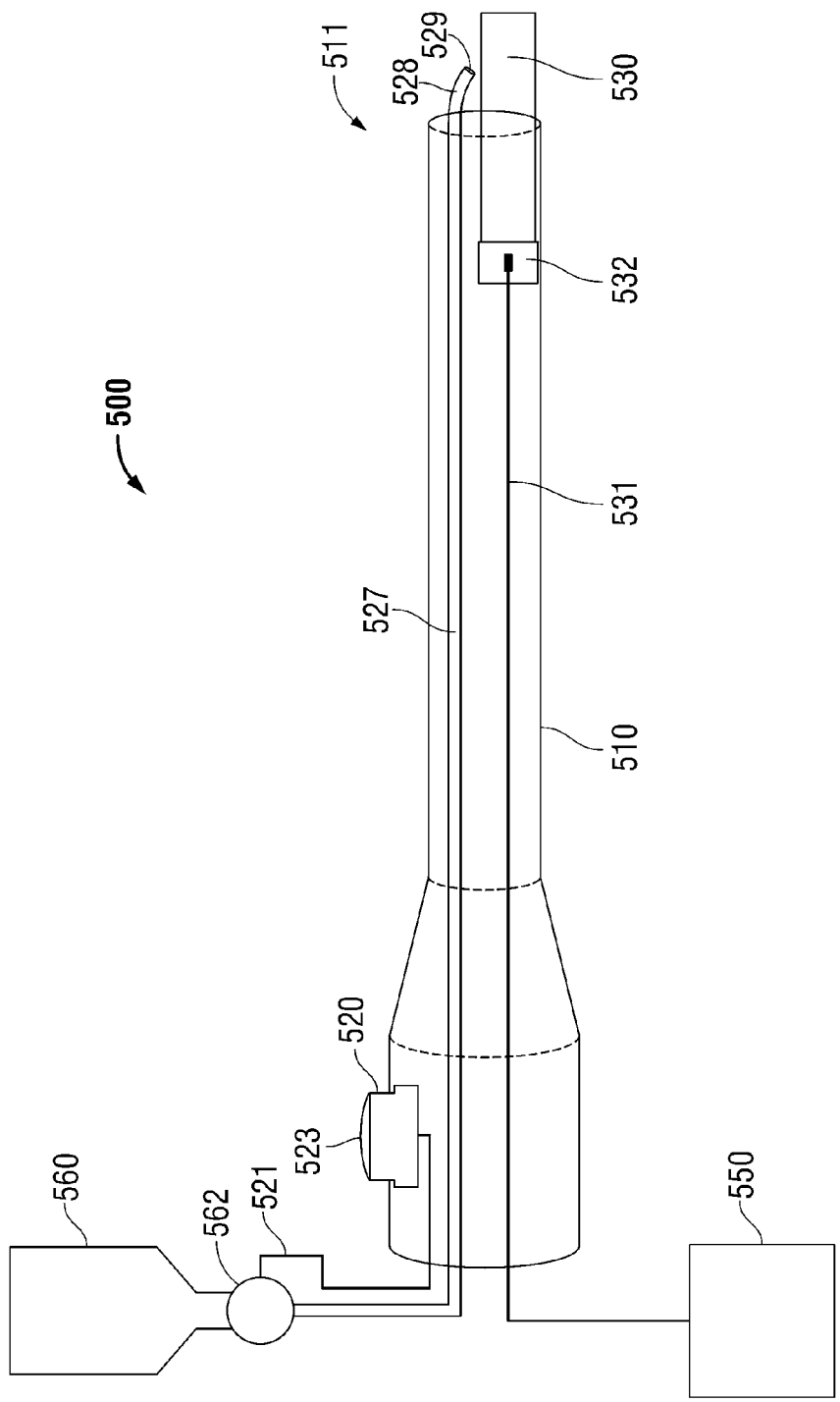
FIG. 5 is an internal view of yet another embodiment of a fluid cooled ultrasonic surgical instrument in accordance with the present disclosure.

Turning now to FIG. 5, yet another embodiment of an ultrasonic surgical system 500 in accordance with the present disclosure is presented that includes an ultrasonic surgical instrument 510 operatively associated with a generator 550 and a coolant source 560. Instrument 510 includes a transducer 532 operatively associated with a waveguide 530, and operatively coupled to generator 550 by conductor 531. A coolant pump 562 is in fluid communication with coolant source 560 and instrument 510 and is configured to pump coolant from coolant supply 560 to instrument 510. Instrument 510 includes a coolant pump switch 520 that is configured to enable a user to selectively enable the delivery of coolant to waveguide 530 and/or a distal end 511 of instrument 510. Coolant pump switch 520 is operably coupled to coolant pump 562 by a conductor 521. Conductor 521 may convey a control signal and/or power to coolant pump 562 to effectuate the operation thereof. Coolant source 560 and/or coolant pump 562 are in fluid communication with a fluid conduit 527 that is configured to direct coolant towards waveguide 530. During use, a user (e.g., surgeon) may enable the flow of coolant by depressing an actuator 523 operatively associated with coolant pump switch 520. Actuator 523 may be a pushbutton, lever, knob, or any other suitable control for enabling and disabling coolant flow. In some embodiments, coolant pump switch 520 may include a continuous actuator, e.g., a rotary or linear controller, to enable a user to continuously vary the speed of fluid pump 562 and, thus, the rate of coolant flow.

Figure 6:
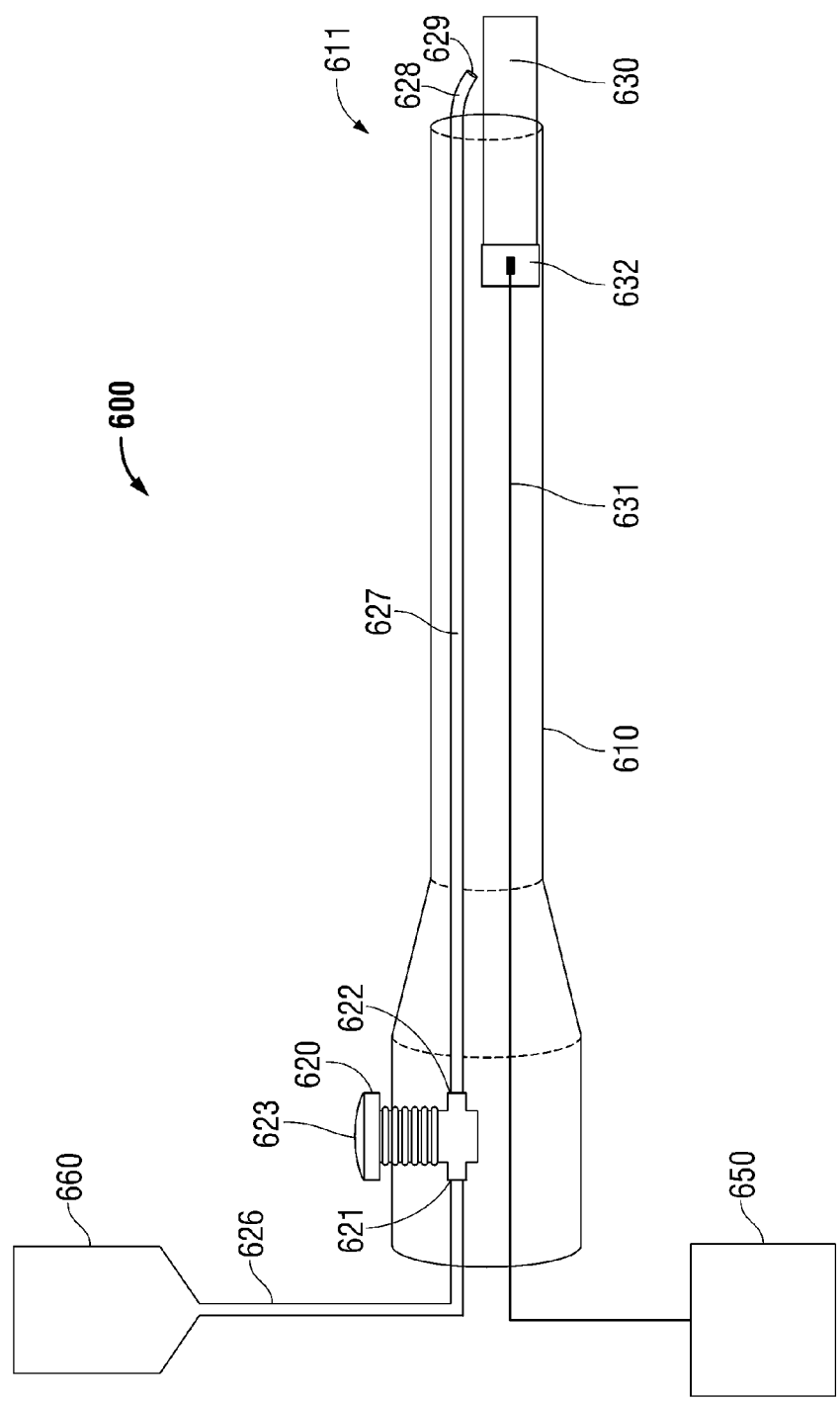
FIG. 6 is an internal view of still another embodiment of a fluid cooled ultrasonic surgical instrument in accordance with the present disclosure.

In yet another embodiment shown in FIG. 6, an ultrasonic surgical system 600 in accordance with the present disclosure includes an ultrasonic surgical instrument 610 operatively associated with a generator 650 and a coolant source 660. Instrument 610 includes a transducer 632 operatively associated with a waveguide 630, and operatively coupled to generator 650 by conductor 631. Instrument 610 includes a coolant pump 660 in fluid communication with coolant source 660 configured to pump coolant from coolant supply 660 to instrument 610. As shown, coolant pump 620 is a manually operated bellows pump that is configured to enable a user to selectively enable the delivery of coolant to waveguide 630 and/or a distal end 611 of instrument 610. Coolant pump 620 includes an inlet 621 in fluid communication with fluid source 660 via a coolant supply conduit 626, and an outlet 622 in fluid communication with a distal end 611 of instrument 610 via a fluid outlet conduit 627. A distal end 628 of fluid outlet conduit 628 includes a coolant outlet port 629 that is configured to direct coolant towards waveguide 630. Advantageously, coolant pump 620 may be of a self-priming design that facilitates the establishment and maintenance of coolant flow. During use, a user (e.g., surgeon) may enable the flow of coolant by repeatedly depressing or "pumping" an actuator 623 operatively associated with coolant pump 620. While a bellows pump is shown in the present embodiment, other suitable pump mechanisms are contemplated within the scope of the present disclosure, including without limitation, a reciprocating pump.

Figure 7:
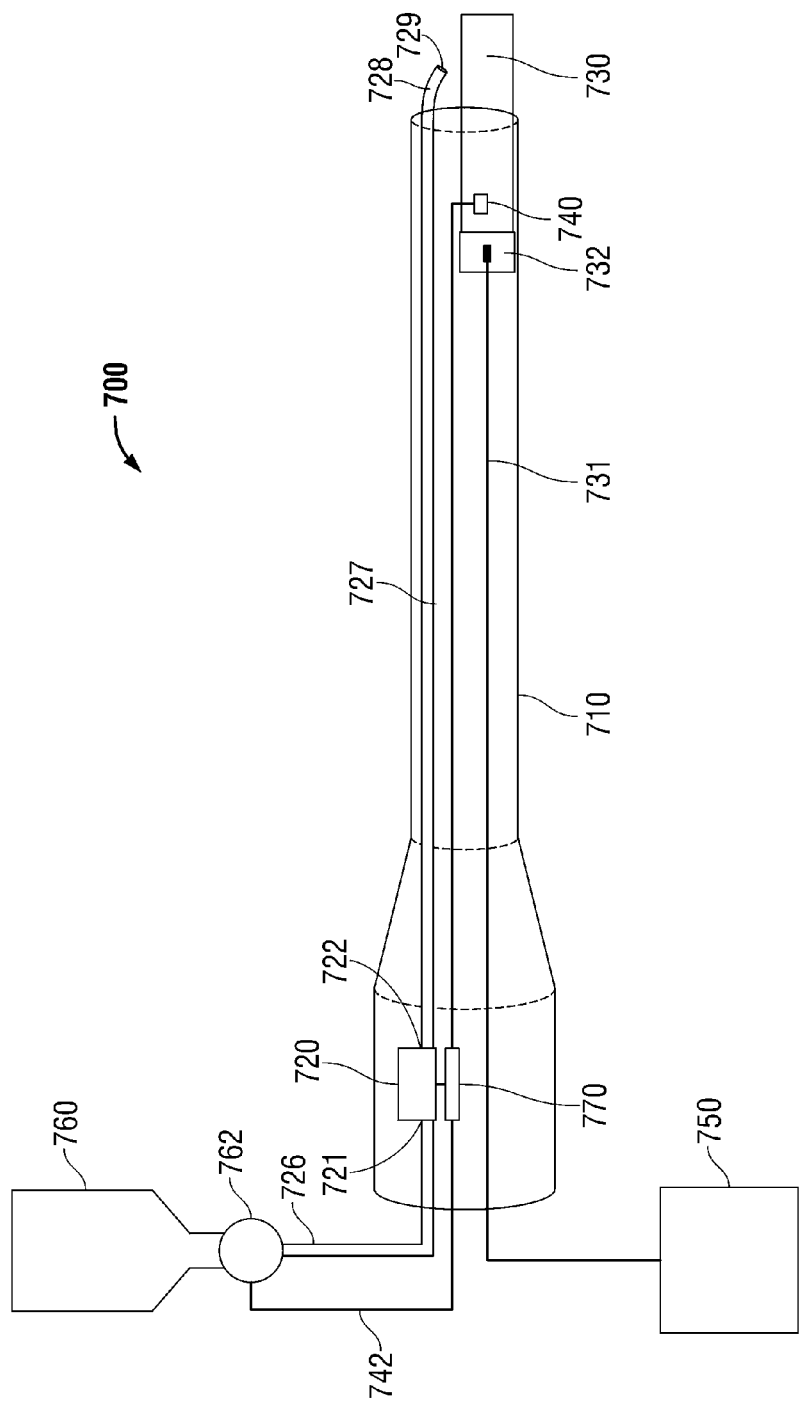
FIG. 7 is an internal view of another embodiment of a fluid cooled ultrasonic surgical instrument in accordance with the present disclosure.

According to still another embodiment shown in FIG. 7, an ultrasonic surgical system 700 in accordance with the present disclosure includes an ultrasonic surgical instrument 710 operatively associated with a generator 750 and a coolant source 760. Instrument 710 includes a transducer 732 operatively associated with a waveguide 730, and operatively coupled to generator 750 by conductor 731. A sensor 740 is operatively associated with waveguide 730 and in operative communication with a controller 770. Controller 770 is in operative communication with a coolant valve 720 and a coolant pump 762. Coolant pump 762 is in fluid communication with coolant source 760 and instrument 710 and is configured to pump coolant from coolant supply 760 to instrument 710. As shown, coolant valve 720 includes an inlet 721 in fluid communication with fluid source 760 and/or pump 762 via a coolant supply conduit 726, and an outlet 722 in fluid communication with a distal end 711 of instrument 710 via a fluid outlet conduit 727. A distal end 728 of fluid outlet conduit 728 includes a coolant outlet port 729 that is configured to direct coolant towards waveguide 730. Coolant valve 720 is configured to respond to a coolant valve control signal received from controller 770 to selectively regulate the delivery of coolant to waveguide 730 and/or a distal end 711 of instrument 710. Coolant pump 762 may additionally or alternatively be configured to respond to a coolant pump control signal from controller 770 to vary a pump parameter, such as pump speed, coolant pressure, and the like. In some embodiments, coolant valve 720 includes a solenoid (not explicitly shown) that is configured to actuate corresponding valve mechanism for regulating coolant flow. In some embodiments, controller may vary a duty cycle of the coolant valve control signal to modulate an average flow of coolant passing through the valve. Controller 770 may be programmed to receive a temperature sensor signal from temperature sensor 740 indicative of a temperature of waveguide 730 and in response thereto, vary at least one of a coolant valve control signal or a coolant pump control signal to achieve a coolant flow sufficient to maintain waveguide 730 within a predetermined temperature range.

The described embodiments of the present disclosure are intended to be illustrative rather than restrictive, and are not intended to represent every embodiment of the present disclosure. The steps of a method disclosed herein may be performed in a different order than that described, and/or the operations performed within an individual step or steps may be desirably be combined into a single step without departing from the scope and spirit of said method. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A method of cooling an ultrasonic surgical instrument, the method comprising:
    insufflating a body cavity of a patient with insufflation media;
    introducing an ultrasonic surgical instrument into the insufflated body cavity;
    activating delivery of ultrasonic energy to the ultrasonic surgical instrument;
    drawing insufflation media from the body cavity into the ultrasonic instrument; and
    moving the insufflation media drawn from the body cavity through the ultrasonic surgical instrument to cool the ultrasonic surgical instrument with the drawn insufflation media.

2. The method according to claim 1, wherein the insufflation media is selected from the group consisting of carbon dioxide, oxygen, air, and saline.

3. The method according to claim 1, wherein insufflation media is moved through the ultrasonic surgical instrument at a rate in accordance with a temperature of the ultrasonic surgical instrument.

4. The method according to claim 1, further comprising:
    sensing a temperature of the ultrasonic surgical instrument;
    determining whether the sensed temperature exceeds a predetermined temperature threshold; and
    moving the insufflation media through the ultrasonic surgical instrument at a rate in accordance with the predetermined temperature threshold.

5. The method according to claim 1, further comprising:
    sensing a temperature of the ultrasonic surgical instrument;
    determining whether the sensed temperature has exceeded a temperature threshold for a predetermined period of time; and
    moving the insufflation media through the ultrasonic surgical instrument at a rate in accordance with the predetermined temperature threshold in response to a determination that the sensed temperature has exceeded a temperature threshold for a predetermined duration of time.

6. The method according to claim 1, further comprising:
sensing a temperature of the ultrasonic surgical instrument;
determining whether the sensed temperature has exceeded a temperature threshold for a predetermined period of time; and
deactivating delivery of ultrasonic energy to the ultrasonic surgical instrument in response to a determination that the sensed temperature has exceeded a temperature threshold for a predetermined duration of time.

7. The method according to claim 1, wherein activating delivery of ultrasonic energy to the ultrasonic surgical instrument includes delivering ultrasonic energy to tissue with a waveguide of the ultrasonic surgical instrument, the waveguide extending distally from a housing of the ultrasonic surgical instrument.

8. The method according to claim 7, wherein moving the insufflation media through the ultrasonic surgical instrument includes expelling the insufflation media over a portion of the waveguide extending distally from the housing of the ultrasonic surgical instrument.

9. A method of cooling an ultrasonic surgical instrument, the method comprising:
positioning an ultrasonic surgical instrument within a body cavity insufflated with an insufflation media;
delivering ultrasonic energy to tissue within the body cavity with a waveguide of the ultrasonic surgical instrument;
drawing insufflation media from the body cavity into a housing of the ultrasonic surgical instrument; and
expelling the insufflation media drawn from the body cavity over the waveguide of the ultrasonic surgical instrument to cool the waveguide.

10. The method according to claim 9, wherein drawing insufflation media from the body cavity into the housing of the ultrasonic surgical instrument includes drawing insufflation media through a coolant inlet port defined in an outer surface of an elongated shaft of the housing of the ultrasonic surgical instrument.

11. The method according to claim 10, wherein expelling the insufflation media drawn from through the coolant inlet port includes expelling the insufflation media over a portion of the waveguide extending from a distal end of the elongated shaft.

12. The method according to claim 11, wherein expelling the insufflation media drawn through the coolant inlet port includes expelling the insufflation media from a coolant outlet port that extends from a distal end of the elongated shaft.

13. The method according to claim 9, wherein drawing insufflation media from the body cavity includes activating a pump positioned in a housing of the ultrasonic surgical instrument to draw insufflation media through a coolant inlet port defined in an outer surface of an elongated shaft that extends from the housing.

14. The method according to claim 13, further comprising sensing a property of the surgical instrument and wherein activating the pump occurs in response to the sensed property exceeding a predetermined threshold.

15. The method according to claim 14, wherein sensing a property of the surgical instrument includes sensing a temperature of the waveguide of the surgical instrument and wherein activating the pump occurs when the sensed temperature of the waveguide is over a predetermined threshold temperature.

16. The method according to claim 13, further comprising sensing a property of the surgical instrument and varying a property of the pump in response to the sensed property.

17. The method according to claim 16, wherein sensing a property of the surgical instrument includes sensing a temperature of the waveguide of the surgical instrument and wherein varying a property of the pump in response to the sensed property includes varying energy supplied to the pump in response to the sensed temperature.

18. The method according to claim 16, further comprising sensing a property of the surgical instrument and preventing delivery of ultrasonic energy to tissue when the sensed property is outside a predetermined range of values.

19. The method according to claim 18, wherein sensing a property of the surgical instrument includes sensing a temperature of the waveguide.

* * * * *